United States Patent [19]

DeVries et al.

[11] Patent Number: 4,777,164

[45] Date of Patent: Oct. 11, 1988

[54] METHOD AND COMPOSITION FOR ENHANCING THE INSECTICIDAL ACTIVITY OF CERTAIN ORGANOPHOSPHORUS COMPOUNDS

[75] Inventors: Donald H. DeVries; Mark J. Costales, both of Concord; Walter Reifschneider, Walnut Creek, all of Calif.

[73] Assignee: The Dow Chemical Company, Midland, Mich.

[21] Appl. No.: 488,897

[22] Filed: Apr. 28, 1983

[51] Int. Cl.⁴ ............................................. A01N 57/00
[52] U.S. Cl. ................................................... 514/89
[58] Field of Search ........................... 424/200; 514/89

[56] References Cited

U.S. PATENT DOCUMENTS

| | | | |
|---|---|---|---|
| 3,244,586 | 4/1966 | Rigterink | 424/200 |
| 3,385,859 | 5/1968 | Rigterink | 260/294.8 |
| 3,669,975 | 6/1972 | Demosay et al. | 424/263 |
| 3,743,648 | 7/1973 | Rigterink | 260/244.8 K |
| 3,794,724 | 2/1974 | O'Melia | 424/200 |
| 4,127,652 | 11/1978 | Maurer | 424/200 |
| 4,223,025 | 9/1980 | Rigterink | 424/200 |
| 4,261,983 | 4/1981 | Maurer et al. | 424/200 |
| 4,325,948 | 4/1982 | Maurer | 424/200 |

OTHER PUBLICATIONS

Ishida et al.; C.A. vol. 60 (1964) 5520e.
Maurer et al.; C.A. vol. 93 (1980) 93:114559q.
Maurer et al.; C.A. vol. 93 (1980) 93:114,700d.
Reifschneider et al.; C.A. vol. 95, 25114q, (1981).

*Primary Examiner*—Allen J. Robinson
*Attorney, Agent, or Firm*—S. Preston Jones; Ronald G. Brookens

[57] ABSTRACT

The insecticidal activity of certain O,O-dialkyl pyridinyl phosphorus ester compounds is enhanced by the admixture therewith of certain substituted pyridinyl phosphoramidates or phosphoramidothioates.

6 Claims, No Drawings

METHOD AND COMPOSITION FOR ENHANCING THE INSECTICIDAL ACTIVITY OF CERTAIN ORGANOPHOSPHORUS COMPOUNDS

BACKGROUND OF THE INVENTION

Organophosphorus compounds are as a group one of the most widely-used insecticides in agriculture. The pyridinyl phosphorus insecticides are a highly active group of compounds used for the kill and control of a great variety of insects.

It has been found, however, that certain pyridinyl phosphorus insecticides are not highly effective in the kill and control of insects of the order Lepidoptera and especially of the genus Heliothis. The reasons for the ineffectiveness of these pyridyl phosphorus insecticides are not fully known nor understood. It is believed that by some mechanism, insects from the above group are insensitive to these phosphorus compounds. Since these insects are of economic importance, methods are continually being sought to increase the activity of these insecticides in the control of insects of the order Lepidoptera.

SUMMARY OF THE INVENTION

The present invention is directed to a method of and compositions for enhancing the insecticidal activity of certain O,O-dialkyl pyridinyl phosphorus ester insecticides which comprises admixing with the pyridinyl phosphorus insecticide, an activity enhancing amount of a substituted pyridinyl phosphoramidate or phosphoramidothioate.

As indicated hereinabove, certain pyridinyl phosphorus insecticides have been found to be ineffective in the kill and control of insects of the order Lepidoptera and especially of the genus Heliothis. This ineffectiveness is not fully known or understood. It has been suggested that by some mechanism, insects from the above group have the ability to detoxify or otherwise inhibit the insecticidal activity of the O,O-dialkyl pyridinyl phosphorus ester compounds.

In order to overcome or bypass this ineffectiveness, prior methods have involved the use of larger treating or dosage amounts of the insecticide or the use of an additional insecticide which is active against insects of the order Lepidoptera. Neither the use of larger dosages nor the use of an additional insecticide has proven to be satisfactory.

The present invention is conducted by contacting insects of the order Lepidoptera and especially the genus Heliothis or their habitat with a composition containing one part of the insecticidally active pyridinyl phosphorus compound to be enhanced and from about 1/16 part to about 16 parts of the substituted pyridinyl phosphoramidate or phosphoramidothioate, i.e., a ratio of about 16:1 to about 1:16. A preferred ratio is from about 8:1 to about 1:1 with the most preferred ratio being from about 8:1 to about 2:1.

The exact mechanism by which the pyridinyl phosphoramido compounds are able to enhance the activity of the O,O-dialkyl pyridinyl phosphorus ester compounds is not fully understood. One theory, for which the applicants do not wish to be bound, suggests that insects of the order Lepidoptera and especially of the genus Heliothis possess an acetylcholinesterase enzyme which is partially insensitive to the pyridinyl phosphorus compounds. The pyridinyl phosphoramidothioates are thought to modify the acetylcholinesterase enzyme such that its sensitivity to pyridinyl phosphorus compounds is increased.

The pyridinyl phosphoramidates and phosphoramidothioates are themselves poor insecticides for Lepidoptera insects but when employed with the O,O-dialkyl pyridinyl phosphorus ester compounds, appear to make insects of the order Lepidoptera susceptible to the insecticidal action of the O,O-dialkyl pyridinyl phosphorus ester compounds.

The O,O-dialkyl pyridinyl phosphorus ester insecticides found to be enhanced by the pyridinyl phosphoramidates or phosphoramidothioates are those which correspond to the formula

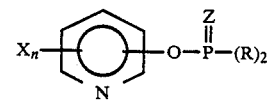

(Formula I)

wherein each X independently represents bromo, chloro, fluoro or iodo; Z represents oxygen or sulfur; R represents alkoxy of 1 to 4 carbon atoms and n represents an integer of from 1 to 3.

The preferred pyridinyl phosphorus insecticides are those compounds wherein X is chloro or fluoro and Z is sulfur. The most preferred insecticides are those compounds wherein X is chloro, n is 3, Z is sulfur and R is methyl or ethyl. These compounds, their methods of preparation and their insecticidal uses are taught in U.S. Pat. No. 3,244,586.

The pyridinyl phosphoramidates and phosphoramidothioates which are employed as activity enhancers are derivatives of substituted pyridinols and correspond to the formula

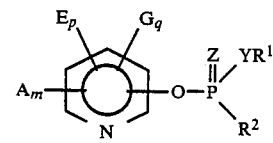

Formula II wherein each A independently represents hydrogen, chloro, bromo or fluoro; each E independently represents alkyl of 1 to 4 carbon atoms, trichloromethyl, trifluoromethyl, cyano, the radical —COOR$^5$ wherein R$^5$ is hydrogen or alkyl of 1 to 4 carbon atoms or the radical R$^6$—S(O)$_d$— wherein R$^6$ is alkyl of 1 to 4 carbon atoms, phenyl substituted with chloro, bromo or fluoro or benzyl and d represents, the same in each occurrence, an integer of 0, 1 or 2; G represents cycloalkyl of 3 or 4 carbon atoms or nitro; m represents an integer of from 0 to 4, inclusive; p represents an integer of 0 to 2, inclusive; q represents an integer of 0 or 1 and the sum of m+p+q=4; R$^1$ represents alkyl of 1 to 4 carbon atoms; R$^2$ represents allylamino, monoalkylamino of 1 to 4 carbon atoms, dialkylamino wherein each alkyl group is independently of 1 to 4 carbon atoms or monocycloalkylamino of 3 to 4 carbon atoms; y is oxygen or sulfur and Z is oxygen or sulfur.

The preferred pyridinyl phosphoramidates and phosphoramidothioates are those wherein Y is oxygen; Z is sulfur; R$^1$ represents alkyl of 1 to 3 carbon atoms; R$^2$ represents monoalkylamino or cyclopropylamino; A represents hydrogen, chloro, fluoro, or trifluoromethyl, and E represents hydrogen or alkylthio.

A most preferred group of the pyridinyl phosphoramidates and phosphoramidothioates include those compounds wherein y is oxygen; Z is sulfur; $R^1$ is ethyl; $R^2$ represents monoalkylamino of 1 to 3 carbon atoms or cyclopropylamino; A represents hydrogen, chloro, fluoro or trifluoromethyl and E represents hydrogen or alkylthio.

In the present specification and claims, the terms "alkyl", "alkoxy", "alkylthio", "dialkylamino" and "monoalkylamino" are employed to designate alkyl, alkoxy, alkylthio, monoalkylamino and dialkylamino radicals wherein the alkyl portion can be either straight or branched chained.

The substituted pyridinyl phosphoramidates and phosphoramidothioates are for the most part known and are taught in U.S. Pat. Nos. 3,244,586; 3,385,859; 3,669,975; 3,743,648; 3,794,724 and 4,223,025.

Those substituted pyridinyl phosphoramidates and phosphoramidothioates compounds which correspond to the above formula can be prepared employing procedures analogous to those taught in said references employing the appropriate starting materials.

In a representative procedure for preparing the substituted pyridinyl phosphoramidates and phosphoramidothioates, substantially equimolar amounts of an appropriate pyridinol reactant corresponding to the formula

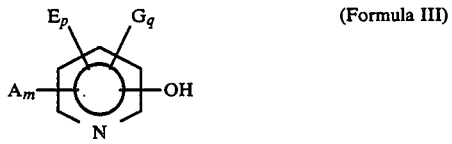

(Formula III)

and an appropriate chlorophosphorus reactant corresponding to the formula

(Formula IV)

are reacted together in the presence of a solvent and a HCl absorber (acid-binding agent) at a temperature in the range of from about 10° C. to about 100° C. This preparative procedure can be represented by the following reaction scheme.

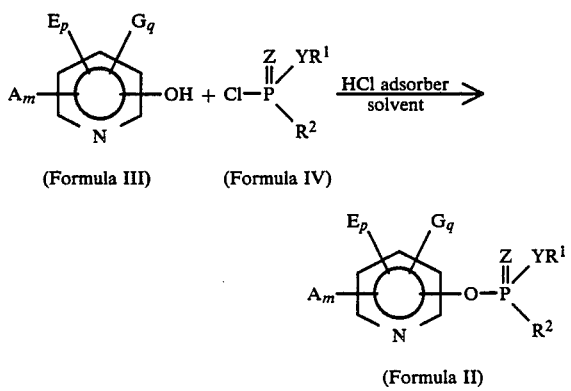

(Formula II)

wherein A, E, G, $R^1$, $R^2$ m, p, q, Y and Z are as hereinbefore defined. No attempt has been made to present a balanced equation.

Representative solvents include those taught in the above references with a preferred solvent being acetonitrile. Representative HCl absorbers include those taught in the above references with a preferred absorber being potassium carbonate. After the completion of the reaction, the insoluble salts are removed by filtration and the filtrate concentrated by evaporation under reduced pressure. The product which remains as a residue is purified by taking up the residue in a solvent such as ether and washing the mixture with a dilute alkaline material such as dilute sodium hydroxide and then with a saturated brine solution such as saturated sodium chloride. The mixture is dried and the solvent removed leaving the desired product.

Preparation of Starting Materials

The N-cyclopropyl O-alkyl phosphoramidochloro compounds corresponding to the formula

(Formula V)

wherein $R^7$ is cycloalkyl of 3 or 4 carbon atoms can be prepared by reacting an alkyl phosphorodichloridothioate or alkyl phosphorodichloridate with a substantially two molar amount of cyclopropylamine in the presence of an inert solvent.

In carrying out this reaction cyclopropylamine is added slowly to a stirred solution of an alkyl phosphorodichloridothioate or an alkyl phosphorodichloridate. The reaction is carried out at a temperature of approximately 0° C. The reaction is complete when all of the phosphorus reactant has been consumed.

Representative solvents include, for example, methylene chloride, ether, benzene, toluene and the like.

At the completion of the reaction, the reaction mixture is filtered to remove precipitated cyclopropylamine hydrochloride and the filtrate is concentrated under reduced pressure. The residue can be used directly or be purified by distillation under vacuum.

Description of Some of the Preferred Embodiments

The following examples illustrate the present invention and the manner by which it can be practiced but, as such, should not be construed as limitations upon the overall scope of the same.

The insecticidal compositions of the present invention are especially effective in killing and controlling insects, particularly Lepidoptera, and especially Heliothis species, which infest crops such as corn, soybeans, tobacco and particularly cotton.

Representative insects of the order Lepidoptera which can be controlled by the practice of the present invention include, for example, but are not limited to, members of the order of Lepidoptera such as the beet armyworm (*Spodoptera exigua*), the Egyptian cotton leafworm (*Spodoptera littoralis*), the black cutworm (*Agrotis ipsilon*), the pink bollworm (*Pectinophora gossypiella*), the codling moth (*Laspeyresia pomonella*) and especially members of the genus Heliothis including the tobacco budworm (*Heliothis virescens*), the corn earworm (*Heliothis zea*) and the American bollworm (*Heliothis armigera*).

Other insects controlled by the practice of the present invention, include, but are not limited to, members of the order Acarina, such as the two-spotted spider mite (*Tetranychus urticae*); members of the order Hemiptera, such as the lygus bug (*Lygus hesperus*); members of the order Coleoptera, such as the cotton boll weevil (*Anthonomus grandis*), the alfalfa weevil (*Hypera postica*), and the Western spotted cucumber beetle (*Diabrotica undecipunctata undecipunctata*); members of the order Diptera, such as the housefly (*Musca domestica*); members of the order Orthoptera, such as the German cockroach (*Blattella germanica*); members of the order Homoptera, such as the aster leafhopper (*Macrosteles fascifrons*) and the cotton aphid (*Aphis gossyppii*).

The mixture of active compounds, i.e., active mixture of the present invention have been found to possess good activity against Heliothis species. Accordingly, the present invention also comprises methods for controlling such insects by applying to said insects and/or their habitats a pesticidally effective amount of the active mixture of compounds. For such uses the unmodified active materials of the present invention can be employed. However, the present invention embraces the use of an insecticidally-effective amount of the active materials in admixture with an inert material, as an adjuvant or carrier therefor, in solid or liquid form. Thus, for example, the active mixture can be dispersed on a finely-divided solid and employed therein as a dust. Also, the active mixture, as liquid concentrates or solid compositions comprising the active mixture, can be dispersed in water, typically with the aid of a wetting agent, and the resulting aqueous dispersion employed as a spray. In other procedures, the active mixture can be employed as a constituent of organic liquid compositions, oil-in-water and water-in-oil emulsions, or water dispersions, with or without the addition of wetting, dispersing or emulsifying agents.

Suitable adjuvants of the foregoing type are well known to those skilled in the art. The methods of applying the solid or liquid pesticidal formulations similarly are well known to the skilled artisan.

As liquid carriers or adjuvants, organic solvents can be employed hydrocarbons, e.g., toluene, xylene, kerosene, diesel fuel, fuel oil, and petroleum naphtha, ketones such as acetone, methyl ethyl ketone and cyclohexanone, chlorinated hydrocarbons such as chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl carbitol acetate and glycerine. Mixtures of water and organic solvents, either as solutions or emulsions, can be employed.

The active mixtures can also be applied as aerosols, e.g., by dispersing them in air by means of a compressed gas such as dichlorodifluoromethane or trichlorofluoromethane and other such materials.

The active mixture of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl groups, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di-(2-ethylhexyl)-ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The active mixture of the present invention can be applied in a formulation which contain about an equal volumetric amount, based on the volume of the active mixture present in said formulation, of (a) a polypropylene glycol having an average molecular weight from about 1,000 to about 5,000; (b) a water insoluble polybutylene glycol; and (c) mixtures and copolymers of (a) and (b). The polypropylene glycols, polybutylene glycols, their mixtures, and co-polymers are all known.

The concentration of the active mixtures in liquid formulations generally is from about 0.01 to about 95 percent by weight or more. Concentrations of from about 0.1 to about 50 weight percent are often employed. In formulations to be employed as concentrates, the active materials can be present in a concentration of from about 5 to about 98 weight percent. In dusts or dry formulations, the concentration of the active ingredient can be from about 0.01 to about 95 weight percent or more; concentrations of from about 0.1 to about 50 weight percent are often conveniently employed. The active compositions can also contain other compatible additaments, for example, plant growth regulants such as herbicides or growth stimulants, pesticides such as insecticides or fungicides and the like.

The present compositions can be applied by the use of powder-dusters, boom and hand sprayers, spray-dusters and by other conventional means. The compositions can also be applied from aircraft as a dust or a spray.

The active mixtures of this invention are usually applied at a rate in the range of from about 1/16 pound to about 5 pounds or more per acre, but lower or higher rates may be appropriate in some cases. A preferred application rate is from ¼ pound to about 2 pounds per acre.

EXAMPLE I

A study was conducted to determine the base-line amount in parts of the compound per million parts of the ultimate composition (ppm) of each of the hereinafter set-forth substituted pyridinyl phosphoramidate and phosphoramidothioates, which correspond to the formula

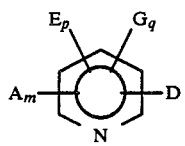

wherein D represents

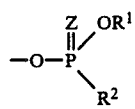

necessary to give at least 95 percent ($LD_{95}$) kill and control of Heliothis larvae.

Test solutions were prepared by admixing predetermined amounts of each of the above compounds in predetermined amounts of water containing predetermined amounts of acetone and Triton X155 surfactant.

The leaves of 5–6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table I.

TABLE I

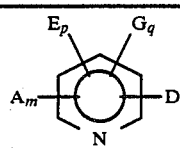

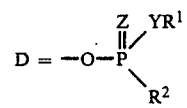

| Compound Number | $A_m$ | $E_p$ | $G_q$ | Ring Position | $YR^1$ | $R^2$ | Z | $LD_{95}$ in ppm |
|---|---|---|---|---|---|---|---|---|
| 1 | — | — | — | 3 | —O—n-P | —NH—n-P | S | >200 |
| 2 | — | 5-Me | — | 2 | —O—n-P | —NH—n-P | S | >200 |
| 3 | — | — | — | 3 | —OMe | —NH—n-P | S | >200 |
| 4 | — | — | — | 4 | —OMe | —NH—i-P | S | >200 |
| 5 | — | — | — | 3 | —OMe | —NH—i-P | S | >200 |
| 6 | — | — | — | 3 | —O—i-P | —NH—i-P | S | |
| 7 | — | — | — | 2 | —O—sec-B | —NH—Me | S | >200 |
| 8 | — | — | — | 2 | —O—i-B | —NH—Me | S | |
| 9 | — | 5-Me | — | 2 | —O—sec-B | —NH—Me | S | |
| 11 | — | — | — | 3 | —OMe | —N(Et)$_2$ | S | >200 |
| 12 | — | 5-Me | — | 2 | —OMe | —NH—Me | S | >200 |
| 13 | — | 5-Me | — | 2 | —OMe | —NH—i-P | S | >200 |
| 14 | — | 5-Me | — | 2 | —OMe | —NH—i-P | S | >200 |
| 15 | — | 5-Cl | — | 2 | —OMe | —NH—i-P | S | >200 |
| 16 | 2-Cl | — | — | 3 | —OMe | —NH—i-P | S | |
| 17 | 3,5-Br$_2$ | — | — | 2 | —OMe | —NH—i-P | S | |
| 18 | — | — | 2-NO$_2$ | 3 | —OMe | —NH—i-P | S | >200 |
| 19 | 3,5-Cl$_2$ | — | — | 2 | —OMe | —NH—i-P | S | |
| 20 | — | — | 5-NO$_2$ | 2 | —OMe | —NH—i-P | S | >200 |
| 21 | 3,5-Br$_2$ | — | — | 4 | —OMe | —NH—i-P | S | |
| 22 | 3,5,6-Cl$_3$ | — | — | 2 | —OMe | —NH—Me | S | |
| 23 | 3,5,6-Cl$_3$ | — | — | 2 | —OEt | —NH—Et | S | >200 |
| 24 | 3,5,6-Cl$_3$ | — | — | 2 | —OMe | —NH—Et | S | >200 |
| 25 | 3,5,6-Cl$_3$ | — | — | 2 | —OEt | —NH—Me | S | |
| 26 | 3,5,6-Cl$_3$ | — | — | 2 | —O—i-P | —NH—Me | S | |
| 27 | 3,5,6-Cl$_3$ | — | — | 2 | —OMe | —NH—n-P | S | >200 |
| 28 | 3,5,6-Cl$_3$ | — | — | 2 | —OMe | —NH—i-P | O | >200 |
| 29 | 2-Br | — | — | 3 | —OMe | —NH—i-P | S | >200 |
| 30 | 3,5,6-Cl$_3$ | — | — | 2 | —OMe | —NH—sec-B | S | >200 |
| 31 | 3,5,6-Cl$_3$ | — | — | 2 | —O—i-P | —NH—Me | S | >200 |
| 33 | — | 2,6-(Me)$_2$ | — | 4 | —OMe | —NH—i-P | S | |
| 34 | 3,5,6-Cl$_3$ | — | — | 2 | —OMe | —N(Me)$_2$ | S | >200 |
| 35 | 3,4,5,6-Cl$_4$ | — | — | 2 | —OMe | —NH—i-P | S | |
| 36 | 3,5-Br$_2$ | — | — | 2 | —OMe | —NH—Me | S | |
| 37 | 3,5-Br$_2$ | — | — | 2 | —OEt | —NH—Me | S | |
| 38 | 3,5-Cl$_2$ | — | — | 2 | —OEt | —NH—Me | S | |

TABLE I-continued

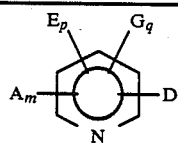

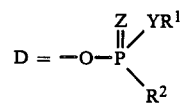

| Compound Number | $A_m$ | $E_p$ | $G_q$ | Ring Position | $YR^1$ | $R^2$ | Z | $LD_{95}$ in ppm |
|---|---|---|---|---|---|---|---|---|
| 39 | 3,5-Cl$_2$ | — | — | 2 | —O—i-B | —NH—Me | S | |
| 40 | 3,5-Cl$_2$ | — | — | 2 | —OMe | —NH—Me | S | |
| 41 | 3,5-Cl$_2$ | — | — | 2 | —OMe | —NH—Et | S | |
| 42 | 3,5-Cl$_2$ | — | — | 2 | —OEt | —NH—Et | S | |
| 43 | 3,5-Cl$_2$ | — | — | 2 | —O—i-P | —NH—Me | S | |
| 44 | 3,5-Br$_2$ | — | — | 2 | —O—i-P | —NH—Me | S | >200 |
| 45 | — | 2,6-(Me)$_2$ | — | 4 | —OMe | —NH—Me | S | |
| 46 | — | 2,6-(Me)$_2$ | — | 4 | —O—i-P | —NH—Me | S | |
| 47 | — | 2,6-(Me)$_2$ | — | 4 | —O—i-B | —NH—Me | S | >200 |
| 48 | — | 2,6-(Me)$_2$ | — | 4 | —OMe | —NH—Et | S | |
| 49 | — | 2,6-(Me)$_2$ | — | 4 | —OEt | —NH—Et | S | >200 |
| 50 | — | 3,5-(Me)$_2$ | — | 2 | —OMe | —NH—i-P | S | >200 |
| 51 | — | 2,6-(Me)$_2$ | — | 4 | —OMe | —NH—n-P | S | >200 |
| 52 | — | 2,6-(Me)$_2$ | — | 4 | —OMe | —NH—sec-B | S | |
| 53 | — | 4,6-(Me)$_2$ | — | 2 | —OEt | —NH—Et | S | >200 |
| 54 | — | 2,3-(Me)$_2$ | — | 4 | —OMe | —NH—i-P | S | >200 |
| 55 | — | 2,5-(Me)$_2$ | — | 4 | —OMe | —NH—i-P | S | >200 |
| 56 | 3,5-Cl$_2$ | — | — | 2 | —O—n-P | —NH—Me | S | |
| 57 | 3,5-Cl$_2$ | — | — | 2 | —O—n-B | —NH—Me | S | |
| 58 | 3,5-Br$_2$ | 4,6-(Me)$_2$ | — | 2 | —OMe | —NH—i-P | S | |
| 59 | 3,5-Cl$_2$ | — | — | 2 | —O—n-P | —NH—n-P | S | |
| 60 | — | 3,5-(Me)$_2$ | — | 2 | —OMe | —NH—i-P | S | |
| 61 | 3,5-Cl$_2$ | — | — | 2 | —O—sec-B | —NH—Me | S | >200 |
| 62 | 3,5-Cl$_2$ | — | — | 2 | —O—i-P | —NH—i-P | S | |
| 63 | 6-Cl | — | — | 2 | —OMe | —NH—i-P | S | |
| 65 | 2,3,6-Cl$_3$ | — | — | 4 | —OMe | —NH—i-P | S | |
| 66 | 3,4,6-Cl$_3$ | — | — | 2 | —OMe | —NH—i-P | S | |
| 67 | 4,6-Cl$_2$ | — | — | 2 | —OMe | —NH—i-P | S | |
| 68 | 5,6-Cl$_2$ | — | — | 2 | —O—n-P | —NH—Me | S | |
| 69 | 3,6-Cl$_2$ | — | — | 2 | —O—n-P | —NH—Me | S | |
| 70 | 3,5-Br$_2$; 6-Cl | — | — | 2 | —OMe | —NH—i-P | S | |
| 71 | 3,5-Br$_2$; 6-Cl | — | — | 2 | —O—i-B | —NH—Me | S | |
| 74 | 5-Br; 3,6-Cl$_2$ | — | — | 2 | —OMe | —NH—i-P | S | |
| 75 | 6-Br; 3,5-Cl$_2$ | — | — | 2 | —OMe | —NH—i-P | S | |
| 76 | 3,5-Br$_2$; 6-Cl | — | — | 2 | —OMe | —NH—i-P | S | >200 |
| 77 | 3-Br; 5-Cl | — | — | 2 | —O—n-P | —NH—Me | S | |
| 78 | 3,5-Br$_2$ | 6-Me | — | 2 | —OMe | —NH—i-P | S | |
| 79 | 2,4,6-Br$_3$; 5-Cl | — | — | 3 | —OMe | —NH—i-P | S | >200 |
| 80 | 3,5-Cl; 6-F | — | — | 2 | —OMe | —NH—i-P | S | |
| 82 | 5-Br; 3-Cl | — | — | 2 | —O—n-P | —NH—Me | S | |
| 83 | 3-Br; 5,6-Cl$_2$ | — | — | 2 | —OMe | —NH—i-P | S | |
| 84 | — | 5-CN | — | 2 | —OMe | —NH—Me | S | |
| 85 | 3,4,5-Cl$_3$ | — | — | 2 | —OMe | —NH—i-P | S | >200 |
| 86 | 3,5-Cl$_2$ | 6-CF$_3$ | — | 2 | —OMe | —NH—i-P | S | |
| 87 | 6-Cl | 4-CF$_3$ | — | 2 | —OMe | —NH—i-P | S | |
| 88 | 6-F | — | — | 2 | —OMe | —NH—i-P | S | |
| 89 | 6-F | — | — | 2 | —OEt | —NH—Et | S | |
| 90 | 6-F | 4-CF$_3$ | — | 2 | —OEt | —NH—Et | S | |
| 91 | 6-Cl | — | — | 2 | —OEt | —NH—Me | S | |
| 92 | 6-Cl | — | — | 2 | —OEt | —NH—i-P | S | |
| 93 | 6-Cl | — | — | 2 | —OEt | —NH—Et | S | >200 |
| 94 | 6-Cl | — | — | 2 | —OEt | —NH—n-P | S | |
| 95 | 6-Cl | — | — | 2 | —OMe | —NH—Et | S | |
| 96 | 6-Cl | — | — | 2 | —OMe | —NH—Me | S | |
| 97 | — | 6-Me | — | 3 | —OEt | —N(Me)$_2$ | S | >200 |
| 98 | — | 6-Me | — | 3 | —SMe | —NH—Me | O | >200 |
| 100 | — | 6-Me | — | 3 | —OEt | —NH—Me | S | >200 |
| 101 | — | 3-Cn | 6-CP | 2 | —OEt | —NH—Et | S | >200 |
| 102 | 3,5,6-Cl$_3$ | — | — | 2 | —SEt | —NH—Et | S | >200 |
| 103 | 3,5-Cl$_2$; 6-F | — | — | 2 | —OEt | —NH—Et | S | >200 |
| 104 | 3,5,6-Cl$_3$ | — | — | 2 | —OEt | —NH—i-P | S | >200 |
| 105 | 6-Cl | 4-CCl$_3$ | — | 2 | —OEt | —NH—Et | S | >200 |
| 106 | — | 5-Me; 6-SMe | — | 3 | —OEt | —NH—Et | S | >200 |
| 107 | 3,5-Br$_2$ | — | — | 4 | —OEt | —NH—Et | S | >200 |
| 108 | 2,6-Br$_2$ | — | — | 3 | —OEt | —NH—Et | S | >200 |

TABLE I-continued $$E_p \quad G_q$$
$$A_m - \underset{N}{\bigcirc} - D$$

$$D = -O - \overset{Z}{\underset{R^2}{P}} \diagup YR^1$$

| Compound Number | $A_m$ | $E_p$ | $G_q$ | Ring Position | $YR^1$ | $R^2$ | Z | $LD_{95}$ in ppm |
|---|---|---|---|---|---|---|---|---|
| 109 | — | 5-Me | — | 3 | —OEt | —NH—Et | S | >200 |
| 110 | 3,5-Cl$_2$ | — | — | 4 | —OEt | —NH—Et | S | >200 |
| 111 | 5-Cl | — | — | 3 | —OEt | —NH—Et | S | >200 |
| 112 | 2-Cl | — | — | 3 | —OEt | —NH—Et | S | >200 |
| 113 | 3,5-Cl$_2$ | 6-S—i-P | — | 2 | —OEt | —NH—Et | S | >200 |
| 114 | 3,5,6-Cl$_3$ | — | — | 2 | —OEt | —NH—Et | O | >200 |
| 115 | 3-Cl | 5-CF$_3$ | — | 2 | —OEt | —NH—Et | S | >200 |
| 117 | 3,5,6-Cl$_3$ | — | — | 2 | —OEt | —NH—Al | S | >200 |
| 118 | 3,5,6-Cl$_3$ | — | — | 2 | —O—i-P | —NH—i-P | S | >200 |
| 119 | — | 5-SO$_2$Et | — | 2 | —OEt | —NH—Et | S | >200 |
| 120 | 3,5-Cl$_2$ | 6-S—Ph | — | 2 | —OEt | —NH—Et | S | >200 |
| 121 | 3,5-Cl$_2$ | 6-S—Be | — | 2 | —OEt | —NH—Et | S | >200 |
| 122 | — | — | 5-NO$_2$ | 2 | —OEt | —NH—Et | S | >200 |
| 123 | — | 5-COOEt | — | 2 | —OEt | —NH—Et | S | >200 |
| 124 | 3,5-Cl$_2$ | 6-S—(4-Cl—Ph) | — | 2 | —OEt | —NH—Et | S | >200 |
| 125 | 5-Cl | — | — | 2 | —OEt | —NH—Et | S | >200 |
| 126 | — | 3,5-(SEt)$_2$ | — | 2 | —OEt | —NH—i-P | S | |
| 127 | 5-Cl | 3-S—n-P | — | 2 | —OEt | —NH—Et | S | |
| 128 | — | 3,5-(CF$_3$)$_2$ | — | 2 | —OEt | —NH—Et | S | |
| 129 | — | 6-CF$_3$ | — | 2 | —OEt | —NH—Et | S | |
| 130 | 3,5-F$_2$ | — | — | 2 | —OEt | —NH—i-P | S | |
| 131 | — | 6-SO—n-B | — | 3 | —O—i-P | —NH—n-B | S | |
| 132 | — | 2,6-(CN)$_2$ | — | 4 | —O—n-B | —NH—Me | S | |
| 133 | — | — | 6-CP | 4 | —O—n-P | —NH—n-B | S | |
| 134 | — | 6-i-P | — | 2 | —OMe | —NH—Me | S | |

CP = cyclopropyl
Me = methyl
Et = ethyl
OMe = methoxy
OEt = ethoxy
O—n-P = n-propoxy
O—i-P = isopropoxy
O—n-B = n-butoxy
O—sec-B = secondary butoxy
O—i-B = isobutoxy
SMe = methylthio
S—i-P = isopropylthio
SEt = ethylthio
S—Ph = phenylthio
S—Be = benzylthio
SO$_2$Et = ethylsulfonyl
SO—n-B = n-butylsulfinyl
NHMe = methylamino
NHEt = ethylamino
NH—i-P = isopropylamino
NH—n-P = n-propylamino
NH—t-B = tert. butylamino
NH—i-B = isobutylamino
NH—AL = allylamino
NH—sec-B = secondary butylamino
NH—n-B = n-butylamino
NH—CP = cyclopropylamino
N(Me)$_2$ = dimethylamino
N(Et)$_2$ = diethylamino

EXAMPLE II

A study was conducted to determine the effectiveness and enhancing response of various combinations of O,O-diethyl O-(3,5,6-trichloro-2-pyridinyl) phosphorothioate and N-ethyl O-(3,5,6-trichloro-2-pyridinyl) O-ethyl phosphoramidothioate (Compound 23) in the control of Heliothis larvae.

Test solutions were prepared by admixing predetermined amounts of each of the above compounds in predetermined amounts of water containing predetermined amounts of acetone and Triton X155 surfactant.

The leaves of 5-6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table II (a and b).

TABLE II(a)

| Compound Tested | Percent Kill and Control of Tobacco Budworm Larvae at Indicated dosage (ppm) | | | |
|---|---|---|---|---|
| | 400 | 200 | 100 | 50 and below |
| Compound A[1] | 93 | 20 | 20 | 0 |
| Compound B[2] | 100 | 60 | 0 | 0 |

TABLE II(b)

| Ratio of Compound A to Compound B | Amount of Compound A + Compound B[4] Percent kill and control of tobacco budworm larvae at indicated dosage (ppm)/ Expected control in parenthesis[3] | | | |
|---|---|---|---|---|
| 10:1 | $\frac{400 + 40}{100\,(93)}$ | $\frac{200 + 20}{100\,(20)}$ | $\frac{100 + 10}{100\,(20)}$ | $\frac{50 + 5}{33\,(13)}$ |
| 5:1 | $\frac{200 + 40}{100\,(20)}$ | $\frac{100 + 20}{100\,(20)}$ | $\frac{50 + 10}{87\,(13)}$ | $\frac{25 + 5}{20\,(0)}$ |
| 2:1 | $\frac{100 + 50}{100\,(20)}$ | $\frac{50 + 25}{93\,(13)}$ | $\frac{25 + 12.5}{80\,(0)}$ | $\frac{12.5 + 6.25}{33\,(0)}$ |
| 1:1 | $\frac{100 + 100}{100\,(30)}$ | $\frac{50 + 50}{100\,(13)}$ | $\frac{25 + 25}{100\,(0)}$ | $\frac{12.5 + 12.5}{27\,(0)}$ |
| 1:2 | $\frac{50 + 100}{100\,(24)}$ | $\frac{25 + 50}{80\,(0)}$ | $\frac{12.5 + 25}{80\,(0)}$ | $\frac{6.25 + 12.5}{27\,(0)}$ |
| 1:5 | $\frac{50 + 250}{100\,(83)}$ | $\frac{25 + 125}{100\,(20)}$ | $\frac{12.5 + 62.5}{100\,(0)}$ | $\frac{6.25 + 31.25}{27\,(0)}$ |
| 1:10 | $\frac{50 + 500}{100\,(100)}$ | $\frac{25 + 250}{100\,(80)}$ | $\frac{12.5 + 125}{100\,(20)}$ | $\frac{6.25 + 62.5}{80\,(0)}$ |

[1] Compound A represents O,O—diethyl O—(3,5,6-trichloro-2-pyridinyl) phosphorothioate.
[2] Compound B represents N—ethyl O—(3,5,6-trichloro-2-pyridinyl) O—ethyl phosphoramidothioate.
[3] Expected control equals % control by Chemical A + % control by Chemical B minus (−) $\frac{\% \text{ control by Chemical A} \times \% \text{ control Chemical B}}{100}$
[4] Percent control obtained for 500, 250, 125, 62.5, 31.25, 25, 12.5 and 6.25 were extrapolated from log-dose probit lines of data from Table II(a).

EXAMPLE III

A study was conducted to determine the effectiveness and enhancing response of various combinations of O,O-dimethyl O-(3,5,6-trichloro-2-pyridinyl) phosphorothioate and N-ethyl O-(3,5,6-trichloro-2-pyridinyl) O-ethyl phosphoramidothioate (Compound 23) in the control of Heliothis larvae.

Test solutions were prepared by admixing predetermined amounts of each of the above compounds in predetermined amounts of water containing predetermined amounts of acetone and Triton X155 surfactant.

The leaves of 5–6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table III.

TABLE III

| Test No. | Chemical[1] | Amount in PPM | Chemical[2] | Amount in PPM | Ratio of A to B | Expected Control in Percent[3] | Actual Control in Percent |
|---|---|---|---|---|---|---|---|
| 1 | A | 12.5 | — | — | — | — | 0 |
| 2 | A | 25 | — | — | — | — | 20 |
| 3 | A | 50 | — | — | — | — | 27 |
| 4 | A | 100 | — | — | — | — | 93 |
| 5 | A | 200 | — | — | — | — | 100 |
| 6 | — | — | B | 12.5 | — | — | 0 |
| 7 | — | — | B | 25 | — | — | 0 |
| 8 | — | — | B | 50 | — | — | 0 |
| 9 | — | — | B | 100 | — | — | 27 |
| 10 | — | — | B | 200 | — | — | 87 |
| 11 | A | 12.5 | B | 12.5 | 1:1 | 0 | 53 |
| 12 | A | 25 | B | 25 | 1:1 | 20 | 93 |
| 13 | A | 50 | B | 50 | 1:1 | 27 | 100 |

In this study it is noted that it requires at least 100 ppm of Chemical A to achieve at least 93 percent control and at least 200 ppm of Chemical B to achieve at least 87 percent control vs. 25 ppm of each of Chemicals A and B together to acheive an equivalent control.
[1] Chemical A represents O,O—dimethyl O—(3,5,6-trichloro-2-pyridinyl) phosphorothioate.
[2] Chemical B represents N—ethyl O—(3,5,6-trichloro-2-pyridinyl) O—ethyl phosphoramidothioate.
[3] Expected control equals % control by chemical A + % control by chemical B minus (−) $\frac{\% \text{ control by chemical A} \times \% \text{ control chemical B}}{100}$

EXAMPLE IV

A study was conducted to determine the effectiveness and enhancing response of various combinations of O,O-diethyl O-(3,5,6-trichloro-2-pyridinyl) phosphorothioate and various phosphoramidothioates of Example I in the control of Heliothis larvae.

Test solutions were prepared by admixing predetermined amounts of O,O-diethyl O-(3,5,6-trichloro-2-pyridinyl) phosphorothioate with a predetermined amount of one of the above indicated phosphoramidothioate compounds in predetermined amounts of water containing predetermined amounts of acetone and Triton X155 surfactant.

The leaves of 5–6 week old cotton seedlings were dipped into one of the above mixtures and allowed to dry. When dry they were removed from the plant and placed into Petri dishes. Five late second instar (approximately 5 day old) tobacco budworm larvae (*Heliothis*

*virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table IV.

TABLE IV

Percent Kill and Control of Tobacco Budworm Larvae With a 1:1 Ratio of O,O—diethyl O—(3,5,6-trichloro-2-pyridinyl) phosphorothioate (200 ppm)* and One of the Indicated Compounds from Example I (200 ppm)

| Compound | % Control | Compound | % Control | Compound | % Control |
|---|---|---|---|---|---|
| 6 | 100 | 66 | 100 | 102 | 100 |
| 8 | 100 | 67 | 100 | 103 | 100 |
| 14 | 100 | 68 | 100 | 104 | 100 |
| 16 | 100 | 69 | 100 | 105 | 100 |
| 17 | 100 | 70 | 100 | 106 | 100 |
| 19 | 100 | 72 | 100 | 107 | 100 |
| 23 | 100 | 74 | 100 | 108 | 100 |
| 24 | 100 | 75 | 100 | 109 | 100 |
| 25 | 100 | 78 | 100 | 110 | 100 |
| 26 | 100 | 80 | 100 | 111 | 100 |
| 30 | 100 | 81 | 80 | 112 | 100 |
| 33 | 100 | 83 | 100 | 114 | 100 |
| 36 | 100 | 86 | 100 | 115 | 100 |
| 37 | 100 | 87 | 100 | 116 | 100 |
| 39 | 100 | 88 | 100 | 117 | 100 |
| 40 | 100 | 89 | 100 | 118 | 100 |
| 41 | 100 | 91 | 100 | 119 | 100 |
| 42 | 100 | 92 | 100 | 120 | 100 |
| 43 | 100 | 93 | 100 | 121 | 100 |
| 44 | 80 | 94 | 100 | 122 | 100 |
| 53 | 100 | 95 | 100 | 123 | 100 |
| 59 | 100 | 96 | 100 | 124 | 80 |
| 62 | 100 | 101 | 100 | 125 | 100 |
| 63 | 100 | | | | |

*At 200 ppm, O,O—diethyl O—(3,5,6-trichloro-2-pyridinyl)phosphorothioate gives 20% kill and control of tobacco budworm larvae.

What is claimed is:

1. An insecticidal composition which comprises an inert carrier and an insecticidally effective amount of an active mixture of toxicants which mixture comprises about 1 part by weight of O,O-diethyl O-(3,5,6-trichloro-2-pyridinyl)phosphorothioate admixture with from about 1/16 part to about 16 parts by weight of N-ethyl O-ethyl O-(3,5,6-trichloro-2-pyridinyl)phosphoramidothioate.

2. The composition as defined in claim 1 wherein the inert carrier is an inert liquid carrier.

3. The composition as defined in claim 2 wherein the active mixture of toxicants is present in an amount of from about 0.01 to about 95 percent by weight of the total composition.

4. The composition as defined in claim 3 wherein the composition is present as an aqueous dispersion and the mixture of toxicants is present in an amount of from about 0.1 to about 50 percent by weight of the total composition.

5. A method for killing and controlling insects of the order Lepidoptera which comprises contacting said insects or their habitat with an insecticidally effective amount of a composition which comprises an inert carrier in intimate admixture with an active mixture of toxicants which mixture comprises about 1 part by weight of O,O-diethyl O-(3,5,6-trichloro-2-pyridinyl)-phosphorothioate in admixture with from about 1/16 part to about 16 parts by weight of N-ethyl O-ethyl O-(3,5,6-trichloro-2-pyridinyl)phosphoramidothioate.

6. The method as defined in claim 5 wherein the composition is employed in amounts of from about 1/16 pound to about 5 pounds per acre.

* * * * *